United States Patent
Calle et al.

(10) Patent No.: US 8,996,120 B1
(45) Date of Patent: Mar. 31, 2015

(54) METHODS AND SYSTEMS OF ADJUSTING ONE OR MORE PERCEIVED ATTRIBUTES OF AN AUDIO SIGNAL

(75) Inventors: Guillermo A. Calle, Moorpark, CA (US); Tracey L. Kruger, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 874 days.

(21) Appl. No.: 12/643,113

(22) Filed: Dec. 21, 2009

Related U.S. Application Data

(60) Provisional application No. 61/139,566, filed on Dec. 20, 2008, provisional application No. 61/160,297, filed on Mar. 14, 2009.

(51) Int. Cl.
*A61N 1/36* (2006.01)
*G06F 19/00* (2011.01)

(52) U.S. Cl.
CPC ..................................... *G06F 19/34* (2013.01)
USPC .......................................................... 607/57

(58) Field of Classification Search
USPC .......................................................... 607/57
See application file for complete search history.

(56) References Cited

U.S. PATENT DOCUMENTS

| | | | | |
|---|---|---|---|---|
| 5,626,629 | A | * | 5/1997 | Faltys et al. ...................... 607/57 |
| 6,052,624 | A | * | 4/2000 | Mann ............................... 607/46 |
| 8,401,656 | B2 | | 3/2013 | Smoorenburg |
| 8,694,113 | B2 | | 4/2014 | Smoorenburg |
| 2007/0255344 | A1 | * | 11/2007 | Van Dijk ........................ 607/57 |
| 2008/0009253 | A1 | * | 1/2008 | Callias et al. .................. 455/205 |

FOREIGN PATENT DOCUMENTS

WO     WO-02054991     7/2002

* cited by examiner

*Primary Examiner* — Alyssa M Alter
(74) *Attorney, Agent, or Firm* — ALG Intellectual Property, LLC

(57) ABSTRACT

An exemplary method of adjusting one or more perceived attributes of an audio signal includes mapping each of the plurality of perceived attributes to one or more control parameters governing an operation of an implantable cochlear stimulator, receiving data representative of an input command to adjust one or more of the perceived attributes, adjusting at least one of the one or more control parameters in response to the received input command and in accordance with the mapping of the perceived attributes to the one or more control parameters, and directing the implantable cochlear stimulator to apply electrical stimulation to one or more stimulation sites within the patient in accordance with the at least one adjusted control parameter. Corresponding methods and systems are also disclosed.

18 Claims, 7 Drawing Sheets

METHODS AND SYSTEMS OF ADJUSTING ONE OR MORE PERCEIVED ATTRIBUTES OF AN AUDIO SIGNAL

RELATED APPLICATIONS

The present application claims priority under 35 U.S.C. §119(e) to U.S. Provisional Patent Application No. 61/139,566 by Guillermo A. Calle et al., filed on Dec. 20, 2008, and entitled "METHODS AND SYSTEMS OF ADJUSTING ONE OR MORE PERCEIVED ATTRIBUTES OF AN AUDIO SIGNAL," and to U.S. Provisional Patent Application No. 61/160,297 by Guillermo A. Calle et al., filed on Mar. 14, 2009, and entitled "METHODS AND SYSTEMS OF ADJUSTING ONE OR MORE PERCEIVED ATTRIBUTES OF AN AUDIO SIGNAL." These applications are incorporated herein by reference in their respective entireties.

BACKGROUND

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that audio signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce audio signals into auditory nerve impulses. People who suffer from sensorineural hearing loss are unable to derive any benefit from conventional hearing aid systems.

To overcome sensorineural hearing loss, numerous cochlear implant systems—or cochlear prosthesis—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, an array of electrodes may be implanted in the cochlea. The electrodes form a number of stimulation channels through which electrical stimulation pulses may be applied directly to auditory nerves within the cochlea. An audio signal may then be presented to a patient by translating the audio signal into a number of electrical stimulation pulses and applying the stimulation pulses directly to auditory nerves within the cochlea via one or more of the electrodes.

When a cochlear implant system is initially implanted in a patient, and during follow-up tests and checkups thereafter, it is usually necessary to fit the cochlear implant system to the patient. Such "fitting" includes adjustment of a variety of control parameters governing the operation of the cochlear implant system to values that are most effective and comfortable for the patient. However, because there could be hundreds of such control parameters to adjust, fitting procedures can be complex, arduous, and costly. Moreover, because a clinician cannot realistically simulate all of the listening situations that the patient may experience, the patient may require several trips to a fitting clinic to obtain a satisfactory result.

SUMMARY

An exemplary method of adjusting one or more perceived attributes of an audio signal includes 1) mapping each of the plurality of perceived attributes to one or more control parameters governing an operation of an implantable cochlear stimulator, 2) receiving data representative of an input command to adjust one or more of the perceived attributes, 3) adjusting at least one of the one or more control parameters in response to the received input command and in accordance with the mapping of the perceived attributes to the one or more control parameters, and 4) directing the implantable cochlear stimulator to apply electrical stimulation to one or more stimulation sites within the patient in accordance with the at least one adjusted control parameter.

Another exemplary method of adjusting one or more perceived attributes of an audio signal includes 1) displaying a graphical user interface configured to facilitate input of one or more commands to adjust a plurality of attributes of an audio signal as perceived by a patient fitted with a cochlear prosthesis, 2) receiving, by way of the graphical user interface, an input command to adjust one or more of the perceived attributes, 3) adjusting one or more control parameters governing an operation of the cochlear prosthesis in response to the input command and in accordance with a predefined mapping of the perceived attributes to the one or more control parameters, and 4) directing the cochlear prosthesis to operate in accordance with the one or more adjusted control parameters.

An exemplary system for adjusting one or more perceived attributes of an audio signal includes an implantable cochlear stimulator configured to apply electrical stimulation representative of an audio signal to one or more stimulation sites within a patient in accordance with a plurality of control parameters and a translation facility communicatively coupled to the implantable cochlear stimulator. The translation facility is configured to 1) map each of a plurality of attributes of an audio signal as perceived by a patient to one or more of the control parameters, 2) receive data representative of an input command to adjust one or more of the perceived attributes, 3) adjust at least one of the control parameters in response to the received input command and in accordance with the mapping of the perceived attributes to the control parameters, and 4) direct the implantable cochlear stimulator to apply electrical stimulation to the one or more stimulation sites in accordance with the at least one adjusted control parameter.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Methods and systems for adjusting one or more attributes of an audio signal as perceived by a cochlear implant patient are described herein. In some examples, an implantable cochlear stimulator is communicatively coupled to a translation facility. The translation facility may be a part of a programming device, a sound processing unit, or any other device as may serve a particular implementation. The implantable cochlear stimulator is configured to apply electrical stimulation representative of an audio signal to a stimulation site within a patient in accordance with one or more control parameters. Exemplary control parameters include, but are not limited to, most comfortable current levels ("M levels"), threshold current levels, channel acoustic gain parameters, front and backend dynamic range parameters, current steering leakage parameters, pulse rate values, pulse width values, filter characteristics, and dynamic compression parameters.

In some examples, the translation facility is configured to adjust one or more of the control parameters in response to a received input command to adjust one or more attributes of the audio signal as perceived by the patient. Exemplary "perceived attributes" may include, but are not limited to, pitch, timbre, quality of sound, lowness, highness, loudness, clarity, intelligibility, lucidity, bass, screeching, reverberation, echo, resonance, booming, and/or any other attribute of an audio signal. The adjustment of the control parameters may be performed in accordance with a predefined mapping of the control parameters to the perceived attributes. In this manner, a patient, clinician, or other user may optimize a performance of a cochlear implant system by adjusting perceived attributes of an audio signal, which, as will be described in more detail below, are easier for a user to understand.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
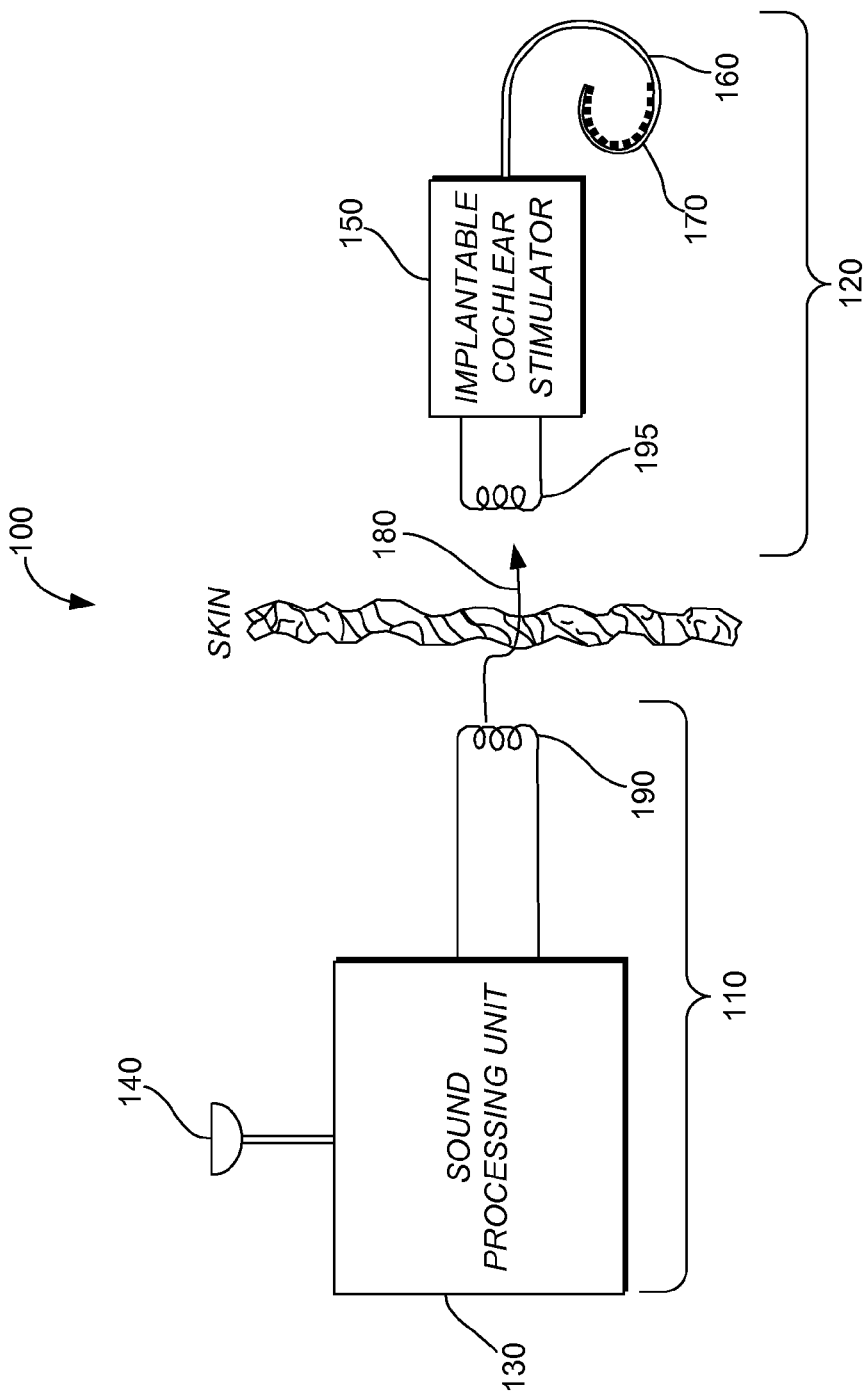
FIG. 1 illustrates an exemplary cochlear implant system according to principles described herein.

To facilitate an understanding of the methods and systems described herein, an exemplary cochlear implant system 100 will now be described in connection with FIG. 1. As shown in FIG. 1, the cochlear implant system 100, also referred to herein as a cochlear prosthesis, includes an external sound processor portion 110 and an cochlear stimulation portion 120 configured to be implanted within a patient. The sound processor portion 110 may include a sound processing unit 130, a microphone 140, and/or additional circuitry as best serves a particular application. The cochlear stimulation portion 120 may include an implantable cochlear stimulator (ICS) 150, a lead 160 with an array of electrodes 170 disposed thereon, and/or additional circuitry as best serves a particular application. It will be recognized that one or more components of the sound processor portion 110 may alternatively be located internal to the patient.

The microphone 140 of FIG. 1 is configured to sense audio signals and convert the sensed signals to corresponding electrical signals. In some examples, the audio signal may include speech. The audio signal may additionally or additionally include music, noise, and/or other sounds. The electrical signals may be transmitted to the sound processing unit 130 by way of an electrical or other suitable link. Alternatively, the microphone 140 may be connected directly to, or integrated with, the sound processing unit 130.

The sound processing unit 130 may include and/or be implemented by any combination of hardware, software, and/or firmware as best serves a particular application. For example, the sound processing unit 130 may include one or more processors, digital signal processors (DSPs), filters, programmable memory units, storage mediums, etc.

In some examples, the sound processing unit 130 may be configured to process the converted audio signals in accordance with a selected sound processing strategy to generate appropriate stimulation parameters for controlling the electrical stimulation generated by the implantable cochlear stimulator 150. The stimulation parameters may control various parameters of the stimulation current applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, spectral tilt, ramp on time, and ramp off time of the stimulation current that is applied to the stimulation site.

The sound processing unit 130 shown in FIG. 1 may be implemented by any suitable combination of components. For example, the sound processing unit 130 may be implemented by a behind-the-ear (BTE) unit configured to be positioned behind the ear. Alternatively, the sound processing unit 130 may be implemented by a portable speech processor (PSP) device, a conventional hearing aid, or any other type of sound processing unit. In certain examples, the sound processing unit 130 may be removed from behind the ear or other operating location by the patient (e.g., prior to sleeping).

The lead 160 of FIG. 1 is adapted to be inserted within a duct of a patient's cochlea. As shown in FIG. 1, the lead 160 includes an array of electrodes 170 disposed along its length. It will be recognized that any number of electrodes 170 may be disposed along the lead 160 as may serve a particular implementation.

Each of the electrodes 170 is electrically coupled to the implantable cochlear stimulator 150. Electronic circuitry within the implantable cochlear stimulator 150 may therefore be configured to apply stimulation current to selected pairs or groups of electrodes 170 in accordance with a specified stimulation pattern controlled by the sound processing unit 130.

As mentioned, the implantable cochlear stimulator 150 and lead 160 may be implanted within the patient, whereas the sound processing unit 130 and the microphone 140 are configured to be located outside the patient, e.g., behind the ear. Hence, the implantable cochlear stimulator 150 and the sound processing unit 130 may be transcutaneously coupled via a suitable data or communications link 180. The communications link 180 allows power and control signals to be transcutaneously sent from the sound processing unit 130 to the implantable cochlear stimulator 150. In some embodiments, data and status signals may also be sent from the implantable cochlear stimulator 150 to the sound processing unit 130.

The external and implantable portions of the cochlear implant system 100 may each include one or more coils configured to transmit and receive power and/or control signals via the data link 180. For example, the external portion 110 of the cochlear implant system 100 may include an external coil 190 and the implantable portion of the cochlear implant system 120 may include an implantable coil 195. The external coil 190 and the implantable coil 195 may be inductively coupled to each other, thereby allowing data and power signals to be wirelessly transmitted between the external portion and the implantable portion of the cochlear implant system 100. Because in certain embodiments, the external portion 110 of the cochlear implant system 100 may not always be within close proximity to the implantable portion of the cochlear implant system 120, such as when the external portion 110 is removed for sleeping, the system may be configured to recognize when the implantable coil 195 and the external coil 190 are within range of one another.

The sound processing unit 130 and the implantable cochlear stimulator 150 may be configured to operate in accordance with one or more control parameters. These control parameters may be configured to specify one or more stimulation parameters, operating parameters, and/or any other parameter as may serve a particular implementation. Exemplary control parameters include, but are not limited to, most comfortable current levels ("M levels"), threshold current levels, channel acoustic gain parameters, front and back-end dynamic range parameters, current steering leakage parameters, pulse rate values, pulse width values, filter characteristics, and dynamic compression parameters. Many other control parameters may be specified as may serve a particular implementation.

In some examples, the control parameters are initially designated during a fitting session during which a clinician or other user adjusts one or more of the control parameters to values that are most effective for the patient. However, because of the sheer number of control parameters that may exist, and because each control parameter may have a plethora of different values, fitting procedures can be complex, arduous, and costly. Moreover, because a clinician cannot realistically simulate all of the listening situations that the patient may experience, the patient may require several trips to a fitting clinic to obtain a satisfactory result.

Adjustment of one or more control parameters may result in a change in one or more attributes of an audio signal as perceived by a patient. These attributes are referred to herein as "perceived attributes" and may include, but are not limited to, pitch, timbre, quality of sound, lowness, highness, loudness, clarity, intelligibility, lucidity, bass, screeching, reverberation, echo, resonance, booming, and/or any other attribute of an audio signal as perceived by a patient as may serve a particular implementation. It is often desirable to adjust one or more of these perceived attributes. Such an adjustment is referred to herein as a "perceptual adjustment". Hence, if a patient desires to adjust a particular perceived attribute (e.g., pitch), a clinician or other user typically has to know which control parameters correspond to the perceived attribute and how to adjust each of the corresponding control parameters in order to realize the desired perceptual adjustment.

Hence, the systems and methods described herein facilitate an effective and intuitive way of optimizing control parameters that govern the operation of a cochlear implant system 100. As will be described in more detail below, one or more control parameters may be mapped to one or more perceived attributes of an audio signal such that receipt of a command to adjust a perceived attribute is configured to automatically adjust one or more control parameters such that the desired perceptual adjustment is realized. In this manner, control parameters governing the operation of a cochlear implant system 110 may be indirectly adjusted and optimized by allowing a clinician, patient, or other user to adjust perceived attributes of an audio signal, which are easier to understand.

Figure 2:
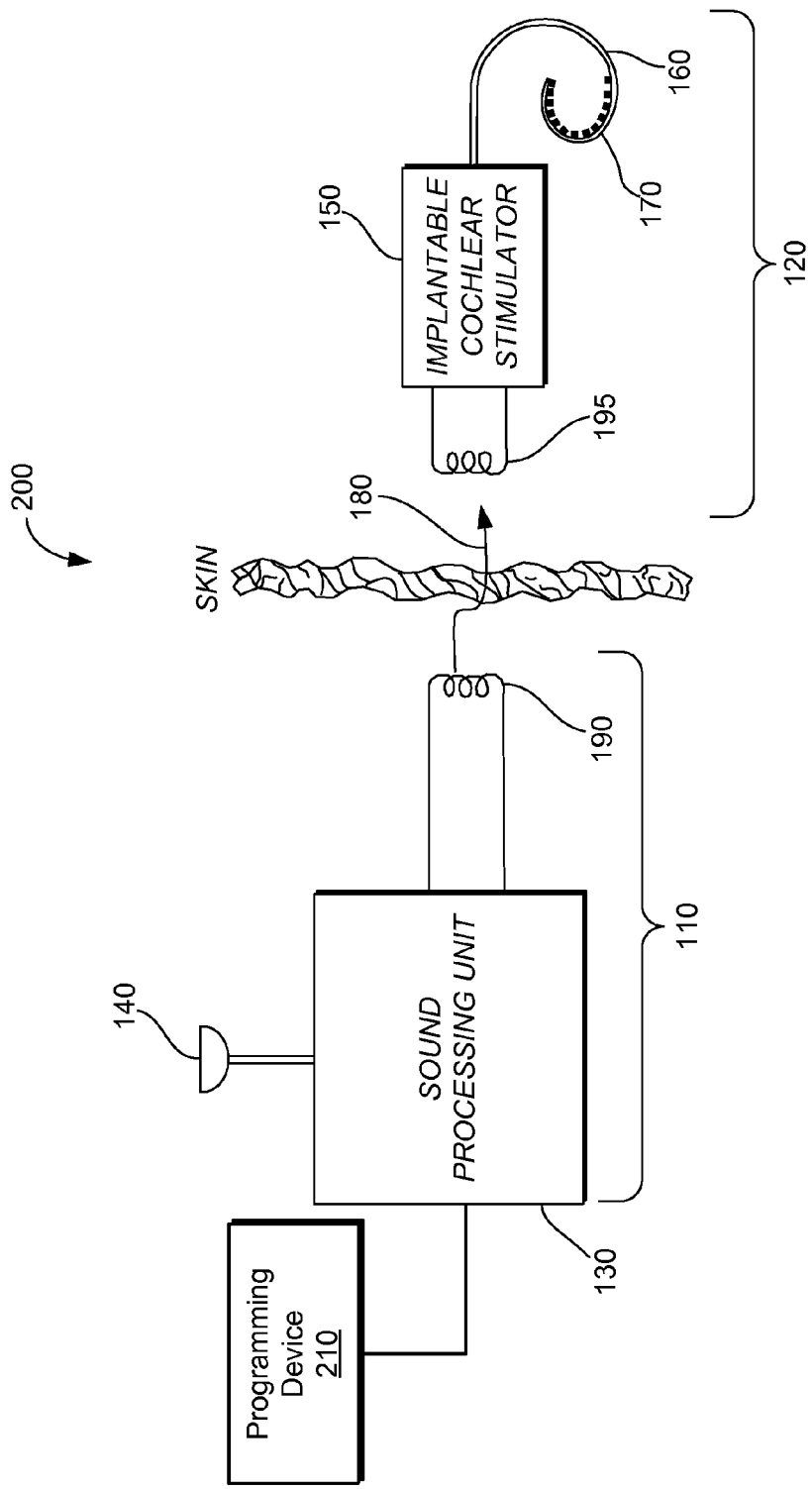
FIG. 2 illustrates an exemplary system configured to facilitate adjustment of one or more control parameters that are mapped to one or more perceived attributes of an audio signal according to principles described herein.

FIG. 2 illustrates an exemplary system 200 configured to facilitate adjustment of one or more control parameters that are mapped to one or more perceived attributes of an audio signal. In some examples, system 200 may include any computer hardware and/or instructions (e.g., software programs), or combinations of software and hardware, configured to perform the processes described herein. In particular, it should be understood that the components of system 200 may be implemented on one physical computing device or may be implemented on more than one physical computing device. Accordingly, system 100 may include any one of a number of computing devices, and may employ any of a number of computer operating systems.

Accordingly, the processes described herein may be implemented at least in part as computer-executable instructions, i.e., instructions executable by one or more computing devices, tangibly embodied in a computer-readable medium. In general, a processor (e.g., a microprocessor) receives instructions, e.g., from a memory, a computer-readable medium, etc., and executes those instructions, thereby performing one or more processes, including one or more of the processes described herein. Such instructions may be stored and transmitted using a variety of known computer-readable media.

A computer-readable medium (also referred to as a processor-readable medium) includes any medium that participates in providing data (e.g., instructions) that may be read by a computer (e.g., by a processor of a computer). Such a medium may take many forms, including, but not limited to, non-volatile media, volatile media, and transmission media. Non-volatile media may include, for example, optical or magnetic disks and other persistent memory. Volatile media may include, for example, dynamic random access memory ("DRAM"), which typically constitutes a main memory. Transmission media may include, for example, coaxial cables, copper wire and fiber optics, including the wires that comprise a system bus coupled to a processor of a computer. Transmission media may include or convey acoustic waves, light waves, and electromagnetic emissions, such as those generated during radio frequency ("RF") and infrared ("IR") data communications. Common forms of computer-readable media include, for example, a CD-ROM, a DVD, any other optical medium, a RAM, a PROM, an EPROM, a FLASH-EEPROM, any other memory chip or cartridge, or any other medium from which a computer can read.

As shown in FIG. 2, a programming device 210 may be selectively and communicatively coupled to the sound processing unit 130. As will be described in more detail below, the programming device 210 may be configured to facilitate mapping of one or more control parameters to one or more perceived attributes of an audio signal, provide an interface configured to facilitate input of one or more commands to adjust one or more perceived attributes, and adjust one or more control parameters in accordance with the mapping in order to realize the requested perceptual adjustments.

Figure 3:
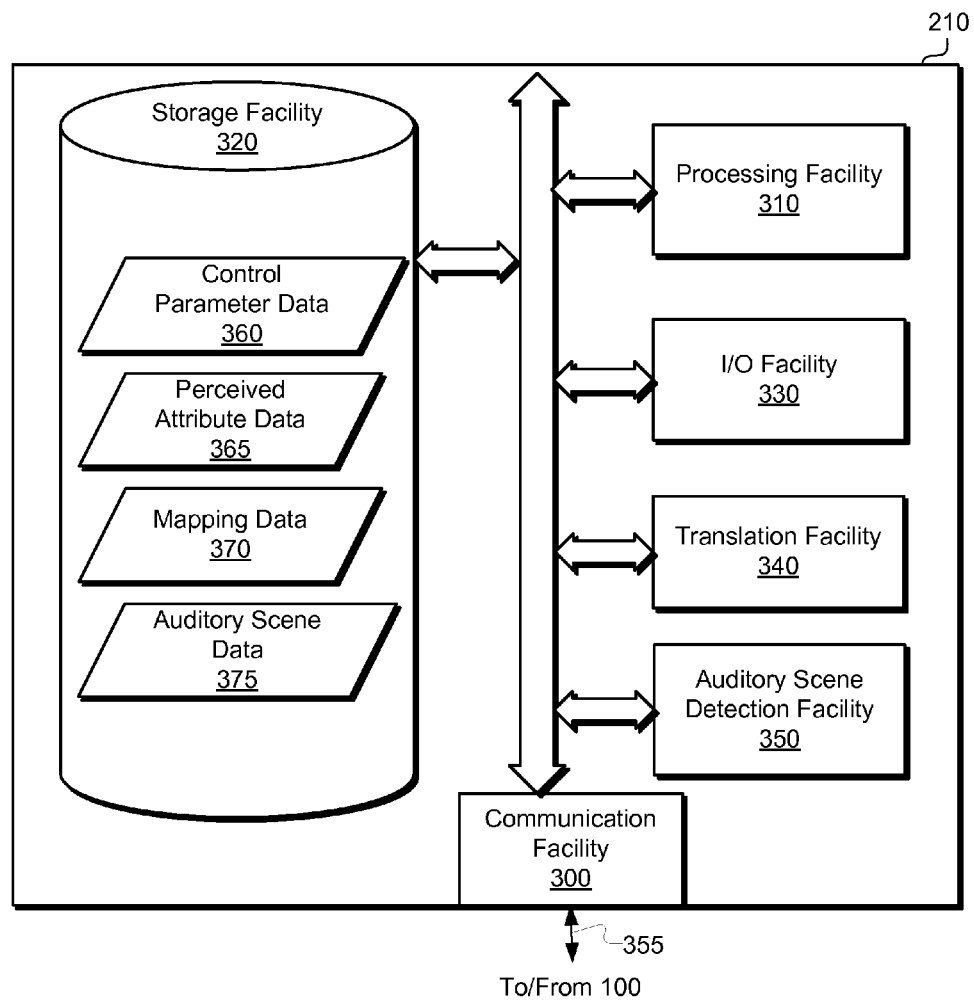
FIG. 3 illustrates components that may be included within an exemplary programming device according to principles described herein.

FIG. 3 illustrates components that may be included within an exemplary programming device 210. The components of programming device 210 may include or be implemented as hardware, computing instructions (e.g., software) embodied on a computer-readable medium, or a combination thereof. While an exemplary programming device 210 is shown in FIG. 3, the exemplary components illustrated in FIG. 3 are not intended to be limiting. Indeed, additional or alternative components and/or implementations may be used.

In general, the programming device 210 may include or be embodied by any device configured to be selectively and communicatively coupled to one or more components of the cochlear implant system 100. For example, the programming device 210 may be selectively and communicatively coupled to the sound processing unit 130. Programming device 210 may also be configured to interact with various peripherals such as a terminal, keyboard, mouse, display screen, printer, stylus, input device(s), output device(s), and/or any other apparatus(es).

As shown in FIG. 3, the programming device 210 may include a communication facility 300, a processing facility 310, a storage facility 320, an input/output ("I/O") facility 330, a translation facility 340, and an auditory scene detection facility 350 communicatively connected to one another. The facilities may be communicatively connected using any suitable technologies. Each of the facilities may be implemented as hardware, computing instructions (e.g., software) tangibly embodied on a computer-readable medium, or a combination of hardware and computing instructions configured to perform one or more of the processes described herein. In certain embodiments, for example, translation facility 340, auditory scene detection facility 350, and/or any of the other facilities may be implemented as one or more software applications embodied on a computer-readable medium such as storage facility 320 and configured to direct processing facility 310 of the programming device 210 and/or the sound processing unit 130 execute one or more of the processes described herein.

Communication facility 300 may be configured to communicate with one or more components of the cochlear implant system 100 (e.g., the sound processing unit 130), including transmitting data representative of control parameters, programming data, etc. to the cochlear implant system 100 and receiving data representative of perceived attribute data, etc. from the cochlear implant system 100. Communication facility 300 may include any device, logic, and/or other technologies suitable for transmitting and receiving such data. Communication facility 300 may be configured to interface with any suitable communication media, protocols, formats, platforms, and networks, including any of those mentioned herein.

Communication interface 300 may be configured to transmit data to and receive data from the sound processing unit 130. Exemplary data transmitted from the programming device 210 to the sound processing unit 130 includes interface commands, programming data, etc. Exemplary data received by the programming device 210 from the sound processing unit 130 includes status data, feedback data, and/or any other type of data as may serve a particular implementation.

In some examples, a communications link 355 may be used to facilitate communication between the programming device 210 and the cochlear implant system 100. The communications link 355 may include any type of link used to transmit data, such as, but not limited to, an RF link, an infrared (IR) link, an optical link, a Bluetooth link, a network link, a thermal link, a wire link, or any other suitable link. In some alternative examples, data acquired by the cochlear implant system 100 may be saved onto a data storage medium (e.g., a flash drive, hard drive, optical disk, etc.) and later read by programming device 210.

Processing facility 310 may be configured to execute and/or direct execution of operations of one or more components of the programming device 210. Processing facility 310 may direct execution of operations in accordance with computer-executable instructions such as may be stored in storage facility 320 or another computer-readable medium. As an example, processing facility 310 may be configured to process perceived attribute data and generate control parameter data based on the perceived attribute data. Processing facility 310 may include any combination of hardware and/or software (e.g., a processor) as may serve a particular implementation.

Storage facility 320 may include one or more data storage media, devices, or configurations and may employ any type, form, and combination of storage media. For example, the storage facility 320 may include, but is not limited to, a hard drive, network drive, flash drive, magnetic disc, optical disc, random access memory ("RAM"), dynamic RAM ("DRAM"), other non-volatile and/or volatile storage unit, or a combination or sub-combination thereof. Data may be temporarily and/or permanently stored in the storage facility 320. In some examples, the storage facility 320 may include or be embodied in a programmable memory unit.

Different types of data may be maintained within storage facility 320 as may serve a particular implementation. For example, control parameter data 360, perceived attribute data 365, mapping data 370, and/or auditory scene data 375 may be maintained by storage facility 320. It will be recognized that data stored within storage facility 320 may additionally or alternatively be stored within any other storage medium as may serve a particular implementation.

Control parameter data 360 may include data representative of one or more control parameters. As mentioned, these control parameters may be configured to specify one or more stimulation parameters, operating parameters, and/or any other parameter governing the operation of the cochlear implant system 100 as may serve a particular implementation. As will be described in more detail below, the control parameter data 360 may be automatically updated or adjusted to effectuate a change in one or more attributes of an audio signal as perceived by a cochlear implant patient.

Perceived attribute data 365 may include data representative of one more attributes of an audio signal as perceived by a cochlear implant patient. The perceived attribute data 365 may be acquired via patient input, one or more sensors, and/or any other input means as may serve a particular implementation.

Mapping data 370 may include data representative of a mapping between one or more control parameters and one or more perceived attributes. As will be described in more detail below, the translation facility 340 may be configured to utilize the mapping data to adjust one or more control parameters to achieve a desired change in one or more perceived attributes.

Auditory scene data 375 may include data representative of one or more auditory scenes that a patient may experience or encounter. As used herein, an "auditory scene" refers to a particular auditory or listening environment of a cochlear implant patient. For example, an auditory scene may be representative of a crowded restaurant, wind, noise from an airplane or automobile, music, a quiet bedroom, and/or any other auditory environment that a cochlear implant patient may experience. The auditory scene data may be acquired via patient input, one or more sensors, and/or any other input mechanism as may serve a particular implementation. As will be described in more detail below, the auditory scene data 375 may be used to optimize one or more control parameters for a particular auditory scene.

In certain embodiments, data 360-375 may be stored using one or more suitable data entities and/or structures, including one or more relational or hierarchical data tables, for example.

I/O facility 330 may be configured to receive user input and provide user output and may include any hardware, firmware, software, or combination thereof supportive of input and output capabilities. For example, I/O facility 330 may include one or more devices for acquiring or otherwise creating data, including, but not limited to, one or more sensors, a microphone, a keyboard or keypad, a mouse, a three-dimensional input device, a joystick, a movement sensor, EEG electrodes, a touch screen component, and/or a receiver (e.g., an RF, Bluetooth, or infrared receiver).

I/O facility 330 may include one or more devices for presenting content for experiencing by a cochlear implant patient, clinician, or other user including, but not limited to, a graphics engine, a display, one or more display drivers, one or more audio speakers, and one or more audio drivers. Accordingly, I/O facility 330 may present content (e.g., one or more graphical user interfaces) for experiencing by a user.

Translation facility 340 may be configured to translate a command input by a user to adjust a perceived attribute into an automatic adjustment of one or more control parameters in order to realize the desired perceptual adjustment. The translation facility 340 may be configured to perform a translation in accordance with a predefined translation heuristic, which may be based on one or more generic, neural network, and/or optimization algorithms. In some examples, the predefined translation heuristic may be updated to reflect changes in patient response to the control parameters.

To facilitate the translation of a command input by a user to adjust a perceived attribute into an automatic adjustment of one or more control parameters, translation facility 340 may map each of a plurality of perceived attributes to one or more control parameters governing an operation of the cochlear implant system (e.g., the sound processing unit 130 and/or the implantable cochlear stimulator 150). Translation facility 340 may perform the mapping in any suitable manner. For example, translation facility 340 may perform the mapping utilizing database analysis, data acquired during training sessions, data acquired during actual patient fitting sessions, and/or any other heuristic or technique as may serve a particular implementation. In some examples, translation facility 340 may perform the mapping ad hoc in response to input provided by one or more programmers and/or clinicians.

Translation facility 340 may be further configured to receive data representative of an input command to adjust one or more of the perceived parameters. The input command may be received by way of a graphical user interface and/or any other input means as will be described in more detail below.

Translation facility 340 may be further configured to adjust at least one of the control parameters in response to the received input command and in accordance with the mapping of the perceived attributes to the one or more control parameters. For example, translation facility 340 may direct sound processing unit 130 to perform the adjustment of the one or more control parameters.

Translation facility 340 may be further configured to direct implantable cochlear stimulator 150 to apply electrical stimulation to one or more stimulation sites within the patient in accordance with the at least one adjusted control parameter. For example, translation facility 340 may cause sound processing unit 130 to transmit the at least one adjusted control parameter to implantable cochlear stimulator 150, which may generate and apply the electrical stimulation in accordance with the at least one adjusted control parameter.

Auditory scene detection facility 350 may be configured to detect one or more auditory scenes and generate auditory scene data 375 accordingly. For example, auditory scene detection facility 350 may detect and record an auditory scene in which the patient is located when an input command to adjust one or more perceived attributes is received. Auditory scene detection facility 350 may then associate the detected auditory scene with one or more control parameters that are adjusted in response to the input command. In this manner, when the patient is again located in the detected auditory scene, auditory scene detection facility 350 may recognize the detected auditory scene and direct translation facility 340 to automatically adjust one or more control parameters accordingly.

The auditory scene detection facility 350 may be configured to operate in accordance with a predefined detection heuristic. For example, the auditory scene detection facility 350 may be configured to use various characterization spectral and/or temporal heuristics to recognize an auditory scene. An example of such a heuristic is a heuristic based on a band-by-band spectral power time variance of the power spectrum. Additionally or alternatively, the auditory scene detection facility 350 may detect an auditory scene by accepting patient input. For example, a patient may recognize a particular auditory scene and input a description of the auditory scene. The auditory scene detection facility 350 may process the input and detect the auditory scene accordingly. In some examples, the auditory scene detection facility 350 may be configured to work in connection with I/O facility 330 (e.g., with a microphone or other sensor) in order to detect an auditory scene.

The programming device 210 may be implemented by any suitable computing device. For example, programming device 210 may be implemented by a fitting station, a personal computer, a handheld device (e.g., a personal digital assistant), a mobile device (e.g., a portable computing device or a mobile telephone), a remote control, and/or any other computing device as may serve a particular implementation. In some examples, the programming device 210 is portable and configured to be carried or worn by the cochlear implant patient. In this manner, the programming device 210 may always be in communication with the sound processing unit 130.

It will be recognized that one or more of the facilities shown to be included within the programming device 210 may additionally or alternatively be included within one or more components of the cochlear implant system 100. For example, at least a portion of the translation facility 340 and/or the auditory scene detection facility 350 may be included within the sound processing unit 130. It will also be recognized that any of the functions performed by the programming device 210 may additionally or alternatively be performed by one or more components of the cochlear implant system 100 (e.g., the sound processing unit 130). Hence, in some embodiments, the cochlear implant system 100 may be configured to perform the methods described herein without the use of a programming device 210 that is separate from the sound processing unit 130.

An exemplary mapping scheme representative of a mapping of one or more control parameters to one or more perceived attributes of an audio signal will now be given in connection with FIG. 4. It will be recognized that the mapping scheme of FIG. 4 is merely illustrative of the many different mappings that may be defined and used by the programming device 210 (e.g., by translation facility 340).

Figure 4:
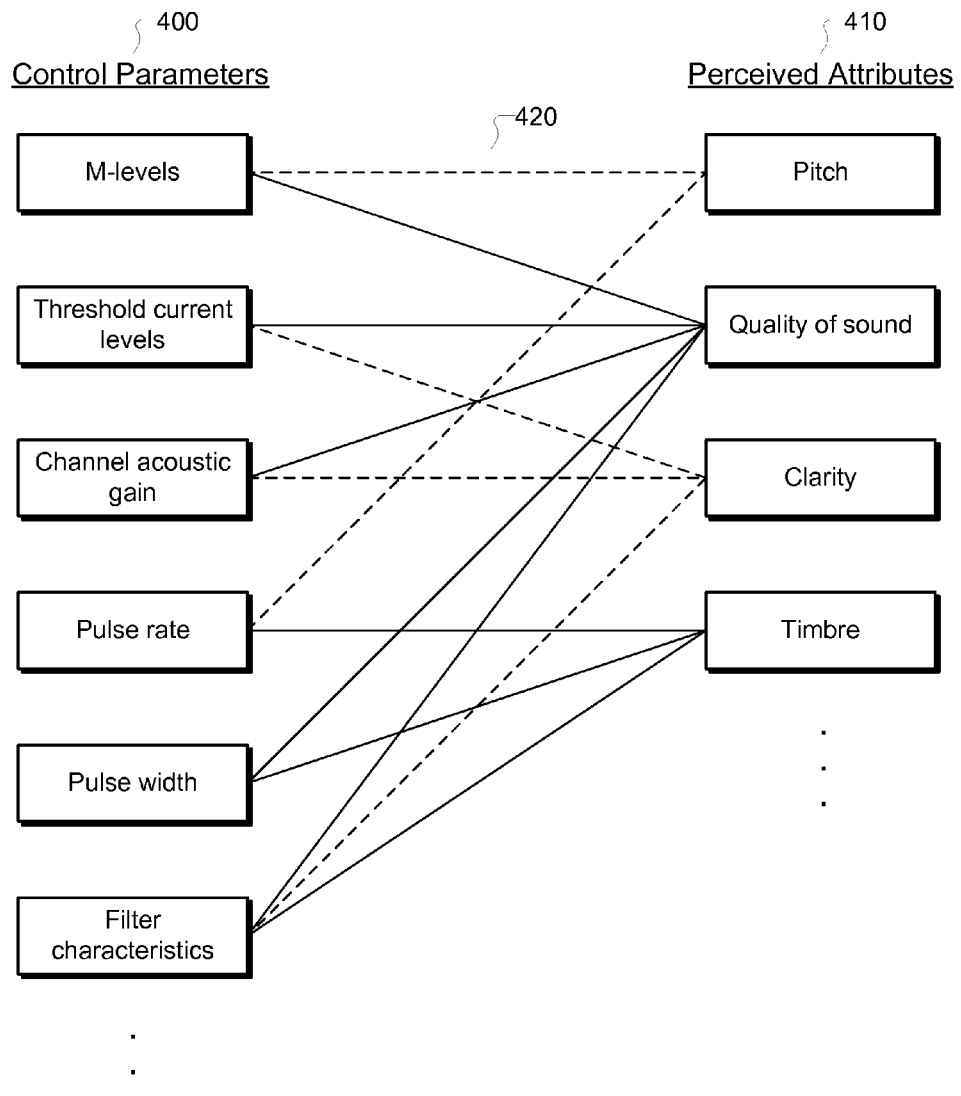
FIG. 4 illustrates an exemplary mapping of one or more control parameters to one or more perceived attributes of an audio signal according to principles described herein.

As shown in FIG. 4, control parameters 400 and perceived attributes 410 are shown to be represented by individual boxes. The particular control parameters 400 and perceived attributes 410 shown in FIG. 4 are merely illustrative of the many different control parameters 400 and perceived attributes 410 that may exist for a particular cochlear implant system 100, audio signal, or patient.

A plurality of lines 420 are shown to interconnect various control parameters 400 and perceived attributes 410. Each line 420 represents a mapping of one of the control parameters 400 to one of the perceived attributes. For example, control parameters "M-levels" and "pulse rate" are mapped to a "pitch" of an audio signal. In other words, manipulation of M-levels and pulse rate may cause a change in pitch of an audio signal as perceived by a patient. Likewise, control parameters "M-levels", "threshold acoustic gain", "channel acoustic gain", "pulse width", and "filter characteristics" are mapped to a "quality of sound" of an audio signal. In other words, adjustment of these control parameters may cause a change in the quality of sound of an audio signal as perceived by a patient. Other mappings are shown for the other perceived attributes listed in FIG. 4. It will be recognized that the mappings shown in FIG. 4 are merely illustrative, and that any of the control parameters 400 may be mapped to any of the perceived attributes 410 as may serve a particular implementation.

With such mappings defined, the translation facility 340 may translate a command to adjust one of the perceived attributes 410 into an automatic adjustment of the control parameter(s) mapped to the perceived attribute 410. This translation may be performed in accordance with a predefined translation heuristic, which may define how each control parameter 400 associated with a particular perceived attribute 410 may be adjusted or manipulated to effectuate a desired change in the perceived attribute 410. For example, the translation heuristic may define how M-levels and pulse rate may be adjusted to effectuate a change in pitch of an audio signal as perceived by a patient.

Figure 5:
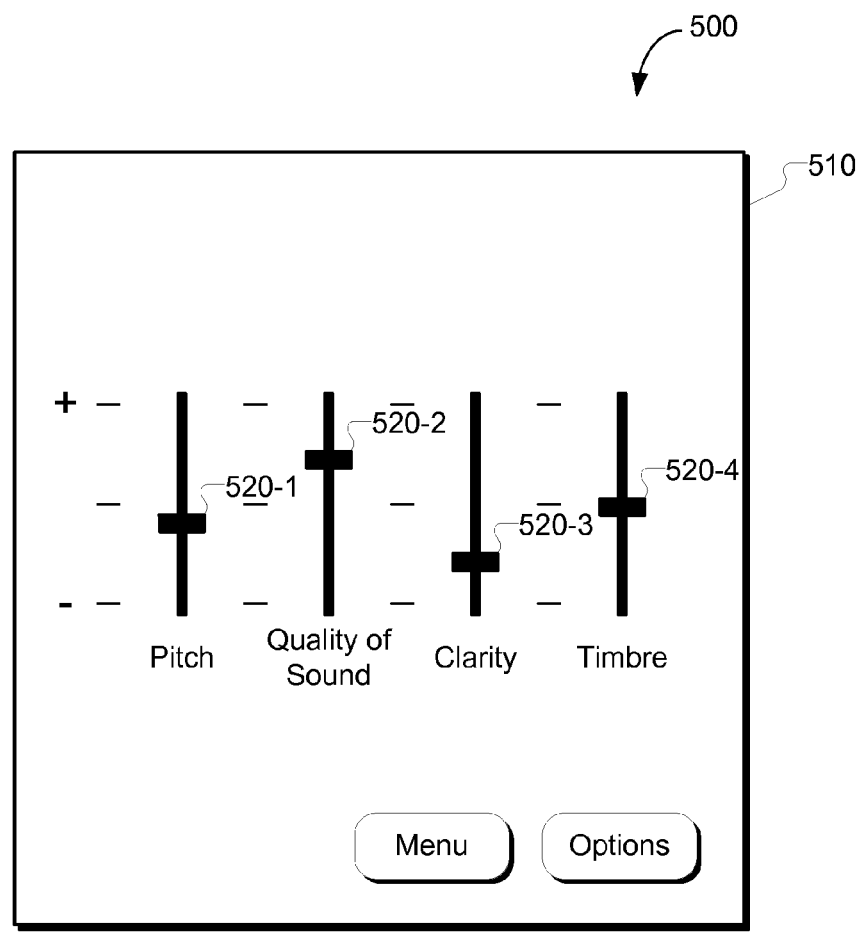
FIG. 5 illustrates an exemplary graphical user interface that may be displayed by a programming device and configured to facilitate input of one or more commands to adjust one or more perceived attributes of an audio signal according to principles described herein.

In some examples, the programming device 210 may be configured to generate and display one or more graphical user interfaces ("GUIs") configured to facilitate input of a command to adjust one or more perceived attributes. For example, FIG. 5 illustrates an exemplary GUI 500 that may be displayed by programming device 210 and configured to facilitate input of one or more commands to adjust one or more perceived attributes of an audio signal. As shown in FIG. 5, the GUI 500 may be displayed within a viewing area 510 (e.g., a display screen associated or a part of the programming device 210). Additionally or alternatively, the GUI 500 may be displayed within a web interface or other display medium.

As shown in FIG. 5, GUI 500 may include one or more slide bars 520 (e.g., slide bars 520-1 through 520-4) configured to facilitate input of one or more commands to adjust one or more perceived attributes. For example, slide bars 520 corresponding to pitch, quality of sound, clarity, and timbre are shown in FIG. 5. Each slide bar 520 may be adjusted by a user to adjust its corresponding perceived attribute. For example, a user may move slide bar 520-1 up or down to increase or decrease the pitch of an audio signal. Slide bars 520-2 through 520-4 may be similarly adjusted in order to adjust a quality of sound, a clarity of an audio signal, and a tone of an audio signal.

It will be recognized that the slide bars 520 shown in FIG. 5 are merely illustrative of the many different input means that may be used to facilitate input one or more commands to adjust one or more perceived attributes. For example, one or more input fields, graphs, and/or other graphical representations may be used to facilitate input of one or more commands to adjust one or more perceived attributes. Additionally or alternatively, the programming device 210 may include or interface with one or more buttons, levers, knobs, keyboards, 3-dimensional input devices, joysticks, movement sensors, and/or other input means configured to facilitate input of one or more commands to adjust one or more perceived attributes.

For example, an input mechanism may be configured to capture one or more patient movements and translate the captured movements into one or more input commands to adjust one or more perceived attributes. To illustrate, the programming device 210 may be configured to recognize movement of a joystick or the like as one or more commands to adjust one or more perceived attributes. For example, an upward movement of the joystick may correspond to a command to increase the loudness of an audio signal, a downward movement of the joystick may correspond to a command to decrease the loudness of the audio signal, a movement of the joystick to the right may correspond to a command to increase a pitch of the audio signal, and a movement of the joystick to the left may correspond to a command to decrease a pitch of the audio signal. It will be recognized that movement of the joystick may be configured to adjust any other perceived attributes of an audio signal as may serve a particular implementation.

As mentioned, a user may experience many different auditory scenes or listening situations. Each of these auditory scenes may affect one or more perceived attributes of an audio signal. For example, varying noise levels across different auditory scenes may affect the pitch, sound quality, loudness, and/or any other attribute of an audio signal as perceived by a patient. Hence, a patient may adjust one or more perceived attributes when experiencing a particular auditory scene in order to optimize his or her perception of an audio signal experienced within the auditory scene.

In some examples, the auditory scene detection facility 350 is configured to detect an auditory scene in which one or more perceived attributes are adjusted to optimal values by a patient. The auditory scene detection facility 350 may then generate auditory scene data 375 representative of the detected auditory scene and associate the control parameters that result in the adjusted perceived attributes with the auditory scene data 375. In this manner, when the patient again experiences the acoustic scene at a later time, the auditory scene detection facility 350 may be configured to recognize the acoustic scene and automatically adjust the control parameters such that the perceived attributes have the optimal values previously designated by the patient.

To illustrate, a patient may adjust one or more perceived attributes of an audio signal to optimal values while in a noisy environment (e.g., a restaurant). The auditory scene detection facility 350 may detect the noisy environment and cause auditory scene data 375 representative of the noisy environment to be stored in storage facility 320. Control parameter data 360 corresponding to the adjusted perceived attributes may also be stored within storage facility 320 and associated with the auditory scene data 375. When the patient again experiences the noisy environment, the auditory scene detection facility 350 may detect the noisy environment and compare the noisy environment to one or more auditory scenes represented by auditory scene data 375 already stored within storage facility 320. If the detected noisy environment matches auditory scene data 375 already stored within storage facility 320, the auditory scene detection facility 350 may automatically adjust the control parameters such that the perceived attributes have the optimal values previously designated by the patient.

The comparison of a detected auditory scene to previously detected auditory scenes may be performed in accordance with a predefined heuristic. In some examples, the auditory scene detection facility 350 may be configured to select a previously detected auditory scene that is the closest match to the detected auditory scene. In this manner, the auditory scene detection facility 350 may be configured to at least partially optimize the control parameters when a new auditory scene is encountered by a patient so that the patient only has to make relatively small adjustments to the perceived attributes.

In some examples, various characteristics of an auditory scene may be mapped to one or more control parameters. In this manner, the auditory scene detection facility 350 may be configured to automatically adjust one or more control parameters when an auditory scene is encountered by a patient, regardless of whether the patient has already encountered the auditory scene. For example, spectral and/or temporal characteristics of wind may be mapped to one or more control parameters that, when adjusted, result in an optimization of one or more perceived attributes of an audio signal presented to a patient in the presence of wind. In this manner, when the auditory scene detection facility 350 detects spectral and/or temporal characteristics of wind, the auditory scene detection facility 350 may be configured to automatically adjust the control parameters in order to optimize one or more perceived attributes of an audio signal presented to the patient in the presence of the wind.

Figure 6:
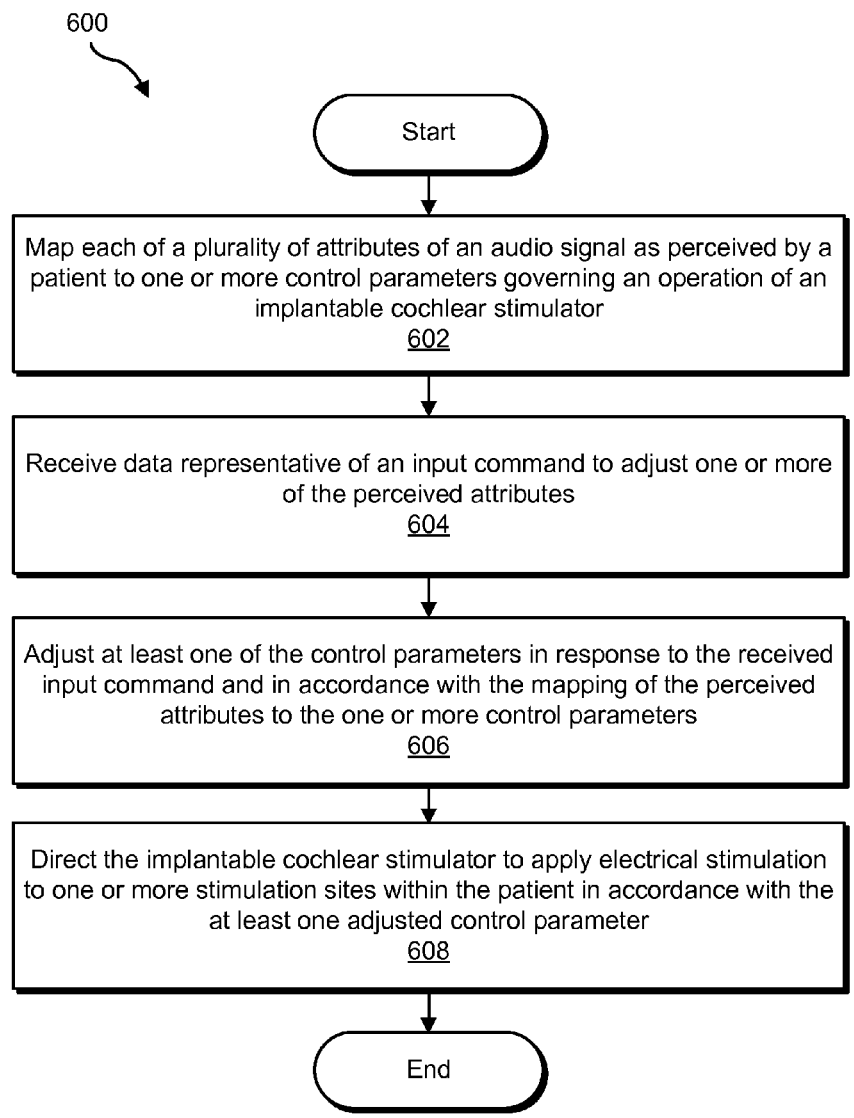
FIG. 6 illustrates an exemplary method of adjusting one or more perceived attributes of an audio signal according to principles described herein.

FIG. 6 illustrates an exemplary method of adjusting one or more perceived attributes of an audio signal. While FIG. 6 illustrates exemplary steps according to one embodiment, other embodiments may omit, add to, reorder, and/or modify any of the steps shown in FIG. 6. One or more of the steps shown in FIG. 6 may be performed by the translation facility 340 and/or any other component described herein.

In step 602, each of a plurality of perceived attributes of an audio signal as perceived by a patient is mapped to one or more control parameters governing an operation of an implantable cochlear stimulator. Translation facility 340 may perform the mapping in any of the ways described herein.

In step 604, data representative of an input command to adjust one or more of the perceived attributes is received. The input command may be received by translation facility 340 in any of the ways described herein. For example, the input command may be received by way of a GUI, a joystick, and/or any other input means may serve a particular implementation.

In step 606, at least one of the control parameters is adjusted in response to the received input command and in accordance with the mapping performed in step 602. Translation facility 340 may adjust the at least one control parameter in any of the ways described herein.

In step 608, the implantable cochlear stimulator is directed to apply electrical stimulation to one or more stimulation sites within the patient in accordance with the at least one adjusted control parameter. Translation facility 340 may direct the implantable cochlear stimulator (e.g., implantable cochlear stimulator 150) to apply electrical stimulation to one or more stimulation sites within a patient in any of the ways described herein.

Figure 7:
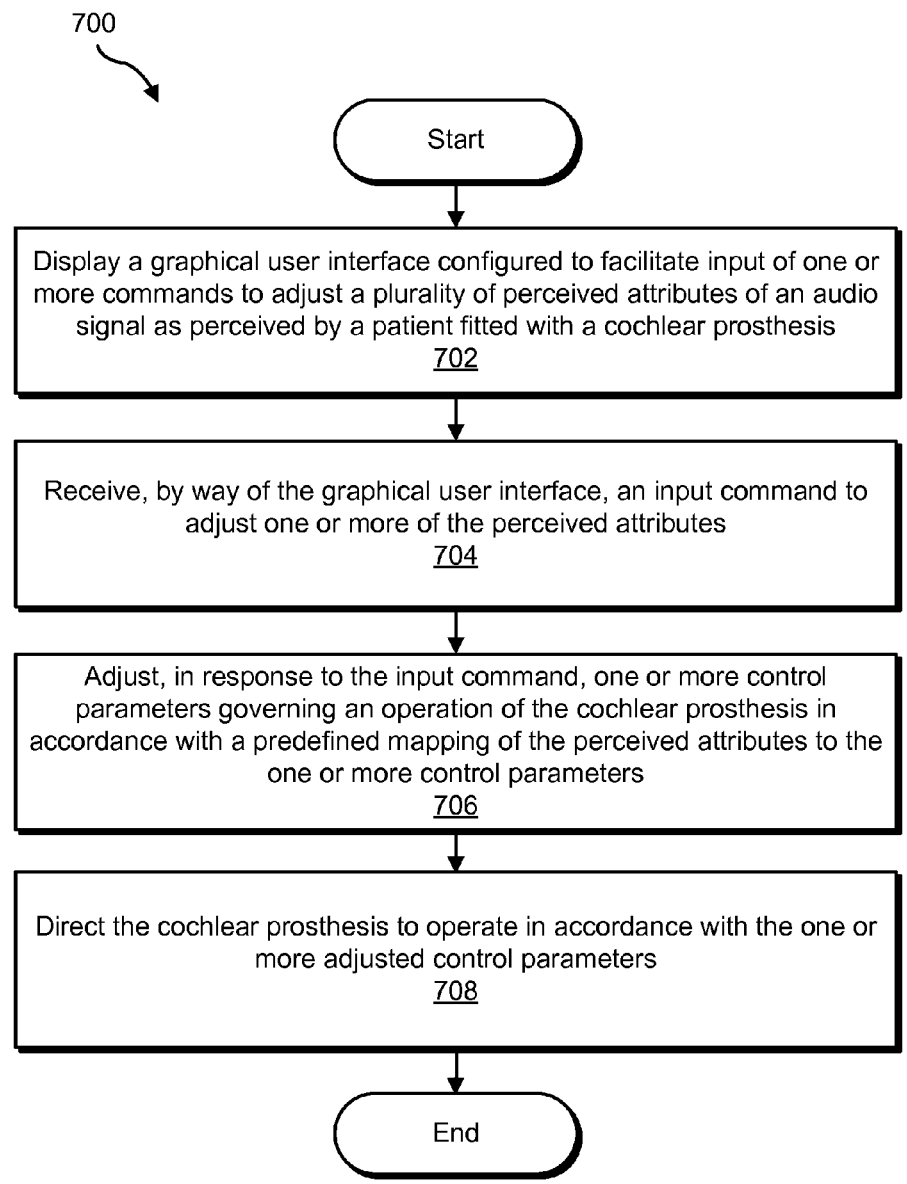
FIG. 7 illustrates another exemplary method of adjusting one or more perceived attributes of an audio signal according to principles described herein.

FIG. 7 illustrates another exemplary method of adjusting one or more perceived attributes of an audio signal. While FIG. 7 illustrates exemplary steps according to one embodiment, other embodiments may omit, add to, reorder, and/or modify any of the steps shown in FIG. 7. One or more of the steps shown in FIG. 7 may be performed by programming device 210 and/or any other component described herein.

In step 702, a graphical user interface is displayed that is configured to facilitate input of one or more commands to adjust a plurality of perceived attributes of an audio signal as perceived by a patient fitted with a cochlear prosthesis. The graphical user interface may be displayed by programming device 210 in any of the ways described herein and may be configured to display any suitable content as may serve a particular implementation.

In step 704, an input command to adjust one or more of the perceived attributes is received by way of the graphical user interface. Programming device 210 may receive the input command in any of the ways described herein.

In step 706, one or more control parameters governing an operation of the cochlear prosthesis are adjusted in response to the input command and in accordance with a predefined mapping of the perceived attributes to the one or more control parameters. Programming device 210 may adjust the one or more control parameters in any of the ways described herein.

In step 708, the cochlear prosthesis is directed to operate in accordance with the one or more adjusted control parameters. For example, programming device 210 may direct sound processing unit 130 and/or implantable cochlear stimulator 150 to operate on accordance with the one or more adjusted control parameters.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method comprising:
    mapping, by a translation facility, a single audible attribute of an audio signal as perceived by a patient to a plurality of electrical control parameters governing an operation of an implantable cochlear stimulator;
    receiving, by the translation facility, data representative of an input command configured to effectuate a desired change in the perceived single audible attribute;
    indirectly adjusting, by the translation facility and based on the mapping of the perceived single audible attribute to the plurality of electrical control parameters, the plurality of electrical control parameters in response to the input command configured to effectuate the desired change in the perceived single audible attribute; and
    directing, by the translation facility, the implantable cochlear stimulator to apply electrical stimulation to one or more stimulation sites within the patient in accordance with the plurality of indirectly adjusted electrical control parameters.

2. The method of claim 1, wherein the indirect adjusting of the plurality of electrical control parameters is configured to optimize the perceived single audible attribute.

3. The method of claim 1, further comprising providing an interface configured to facilitate input of the input command.

4. The method of claim 3, wherein the interface comprises a graphical user interface.

5. The method of claim 1, further comprising capturing at least one movement of a user and translating the captured movement into the input command.

6. The method of claim 5, wherein the at least one captured movement is generated with a joystick.

7. The method of claim 1, wherein the indirect adjusting of the plurality of electrical control parameters is performed in accordance with a predefined translation heuristic.

8. The method of claim 7, wherein the predefined translation heuristic is based at least in part on one or more of a generic algorithm, a neural network algorithm, and an optimization algorithm.

9. The method of claim 1, wherein the plurality of electrical control parameters comprise at least one of a comfortable current level, a threshold current level, a channel acoustic gain parameter, a front dynamic range parameter, a back dynamic range parameter, a current steering leakage parameter, a pulse rate, a pulse width, a filter characteristic, and a dynamic compression parameter.

10. The method of claim 1, wherein the perceived single audible attribute comprises a pitch, a timbre, a quality of sound, a lowness, a highness, a loudness, a clarity, an intelligibility, a lucidity, a bass, a screeching, a reverberation, an echo, a resonance, or a booming of the audio signal as perceived by the patient.

11. The method of claim 1, further comprising:
detecting, by an auditory scene detection facility, an auditory scene in which the patient is located when the input command is received; and
associating the plurality of indirectly adjusted electrical control parameters with the detected auditory scene.

12. The method of claim 11, further comprising automatically utilizing, by the translation facility, the plurality of indirectly adjusted electrical control parameters associated with the detected auditory scene when the patient is again located in the detected auditory scene.

13. The method of claim 1, wherein the translation facility is implemented by a programming device communicatively coupled to a sound processing unit that is configured to direct an operation of the implantable cochlear stimulator.

14. The method of claim 1, wherein the translation facility is included within a sound processing unit configured to direct an operation of the implantable cochlear stimulator.

15. A system comprising:
an implantable cochlear stimulator configured to apply electrical stimulation representative of an audio signal to one or more stimulation sites within a patient in accordance with a plurality of electrical control parameters; and
a translation facility communicatively coupled to the implantable cochlear stimulator and configured to
map a single audible attribute of an audio signal as perceived by a patient to the plurality of electrical control parameters,
receive data representative of an input command configured to effectuate a desired change in the perceived single audible attribute,
indirectly adjust, based on the mapping of the perceived single audible attribute to the plurality of electrical control parameters, the plurality of the electrical control parameters in response to the input command configured to effectuate the desired change in the perceived single audible attribute, and
direct the implantable cochlear stimulator to apply electrical stimulation to the one or more stimulation sites in accordance with the plurality of indirectly adjusted electrical control parameters.

16. The system of claim 15, further comprising:
a sound processing unit communicatively coupled to the implantable cochlear stimulator and configured to generate the plurality of electrical control parameters; and
a programming device selectively and communicatively coupled to the sound processing unit and configured to include the translation facility.

17. The system of claim 15, further comprising a sound processing unit communicatively coupled to the implantable cochlear stimulator, wherein the translation facility is included within the sound processing unit.

18. The system of claim 15, further comprising an auditory scene detection facility communicatively coupled to the implantable cochlear stimulator, the auditory scene detection facility being configured to:
detect an auditory scene in which the patient is located with the input command is received; and
associate the plurality of indirectly adjusted electrical control parameters with the detected auditory scene.

* * * * *